US009347895B2

(12) United States Patent
Yasukawa (10) Patent No.: US 9,347,895 B2
(45) Date of Patent: May 24, 2016

(54) X-RAY DIFFRACTION APPARATUS, X-RAY DIFFRACTION MEASURING METHOD, AND CONTROL PROGRAM

(71) Applicant: Rigaku Corporation, Tokyo (JP)

(72) Inventor: Shoichi Yasukawa, Tokyo (JP)

(73) Assignee: RIGAKU CORPORATION, Tokyo (JP)

( * ) Notice: Subject to any disclaimer, the term of this patent is extended or adjusted under 35 U.S.C. 154(b) by 281 days.

(21) Appl. No.: 14/196,768

(22) Filed: Mar. 4, 2014

(65) Prior Publication Data

US 2014/0314206 A1 Oct. 23, 2014

(30) Foreign Application Priority Data

Apr. 17, 2013 (JP) ................................. 2013-086740

(51) Int. Cl.
*G01N 23/20* (2006.01)
*G01N 23/205* (2006.01)

(52) U.S. Cl.
CPC .................... *G01N 23/205* (2013.01)

(58) Field of Classification Search
CPC ....... G01N 23/00; G01N 23/02; G01N 23/04; G01N 23/043; G01N 23/046; G01N 23/06; G01N 23/063; G01N 23/083; G01N 23/0872; G01N 23/20016; G01N 23/20025; G01N 23/20075
USPC ........... 378/71, 72, 73, 79, 81, 82, 83, 84, 86, 378/87, 88
See application file for complete search history.

(56) References Cited

U.S. PATENT DOCUMENTS

| 6,813,338 B2 | 11/2004 | Takata et al. | |
|---|---|---|---|
| 2003/0091147 A1 | 5/2003 | Takata et al. | |
| 2003/0231737 A1* | 12/2003 | Omote | G21K 1/02 378/19 |
| 2013/0103339 A1* | 4/2013 | Durst | G01N 23/207 702/104 |
| 2013/0336454 A1* | 12/2013 | Nomura | G01N 23/20025 378/79 |

FOREIGN PATENT DOCUMENTS

| JP | 8-338818 A | 12/1996 |
|---|---|---|
| JP | 2003-75373 A | 3/2003 |
| JP | 2003-149180 A | 5/2003 |

OTHER PUBLICATIONS

Broennimann et al., "The PILATUS 1M detector", Journal of Synchrotron Radiation, vol. 13, pp. 120-130, Nov. 22, 2005.

(Continued)

*Primary Examiner* — Nicole Ippolito
*Assistant Examiner* — Jason McCormack
(74) *Attorney, Agent, or Firm* — Birch, Stewart, Kolasch & Birch, LLP (57) ABSTRACT

The X-ray diffraction apparatus irradiates a sample with an X-ray and performs frame photographing in each X-ray diffraction angle, and includes a control section (141) controlling the frame photographing by scanning without closing a shutter, a data acquisition section (142) acquiring detection data of each frame which has been detected by a semiconductor pixel detector in the frame photographing, a frame integration section (146) integrating the detection data which has been acquired in each scanning for each frame, and a determination section (147) determining whether the integrated detection data has a sufficient intensity or not, and the control section (141) controls so as to finish measurement when the integrated detection data has a sufficient intensity and so as to perform the scanning again when the integrated detection data does not have a sufficient intensity.

6 Claims, 11 Drawing Sheets

(56) References Cited

OTHER PUBLICATIONS

Hasegawa et al., "Development of a shutterless continuous rotation method using an X-ray CMOS detector for protein crystallography", Journal of Applied Crystallography, vol. 42, pp. 1165-1175, Oct. 14, 2009.

Hulsen et al., "Protein crystallography with a novel large-area pixel detector", Journal of Applied Crystallography, vol. 39, pp. 550-557, May 5, 2006.

S. Kozaki, "Automatic Search Match of X-ray Diffraction Data", Progress of X-ray Analysis XIII, Japan Kagaku Gijutsu-Sha, pp. 47, Nov. 20, 1981.

* cited by examiner

| Exposure Time | Rmerge | AVERAGE INTENSITY | R (>2σ) |
|---|---|---|---|
| 16 sec/frame n= 50.0 | 2.48% | 30136 | 2.82% |
| 16 sec/frame n = 32.0 | 2.40% | 19136 | 2.99% |
| 8 sec/frame n = 64.0 | 3.25% | 18934 | 3.68% |

X-RAY DIFFRACTION APPARATUS, X-RAY DIFFRACTION MEASURING METHOD, AND CONTROL PROGRAM

BACKGROUND OF THE INVENTION

1. Field of the Invention

The present invention relates to an X-ray diffraction apparatus which irradiates a sample with an X-ray and performs frame photographing in each angle range, an X-ray diffraction measuring method, and a control program.

2. Description of the Related Art

In the frame photographing for X-ray single crystal structure analysis, it is necessary to set an X-ray exposure time for one frame. This exposure time needs to be adjusted by a user according to sample crystalline property, X-ray source strength, and detector sensitivity. Conventionally, a user set the exposure time with reference to a default exposure time set on software or according to his experience, and controlled an apparatus to measure a diffracted X-ray. If the exposure time is short, sufficient diffraction intensity is not obtained, and therefore the analysis result is degraded and the measurement is performed again in this case. On the other hand, if the exposure time is unnecessarily long, the time required for the measurement becomes long.

Figure 10:
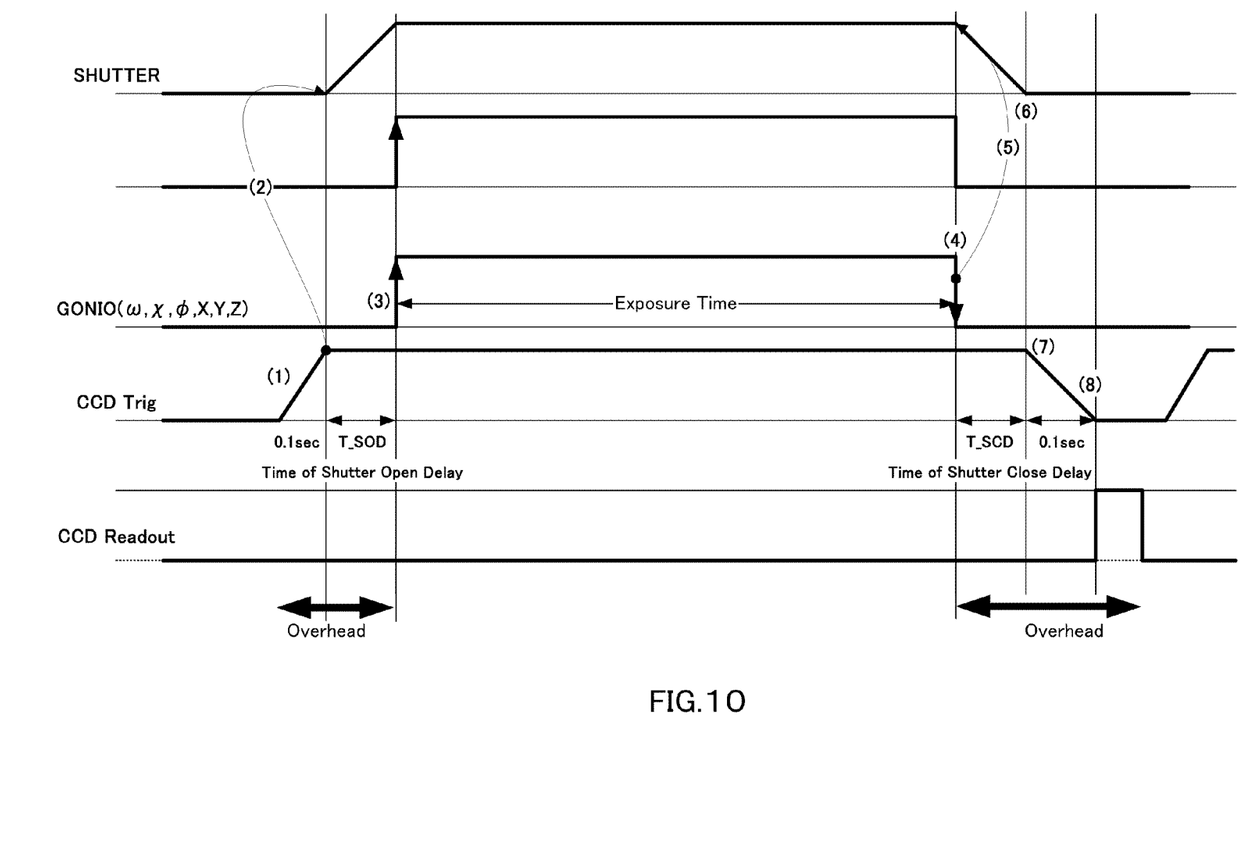
FIG. 10 is a diagram showing a conventional measurement sequence for one frame.

Further, in a CCD or an IP detector which is used in such diffracted X-ray measurement, it is necessary to control open and close of a shutter for the frame exposure, and shutter-less measurement which makes the shutter control unnecessary cannot be realized. FIG. 10 is a diagram showing a conventional measurement sequence for one frame. In the example shown in FIG. 10, shutter control, goniometer control, CCD detection, and CCD read-out are performed in the order from (1) to (8). Then, overhead times are generated before and after the frame photographing for the shutter open and close operation.

In a semiconductor pixel detector, however, since the read-out time is less than several milliseconds for each frame, it has become possible to carry out continuous scan measurement while keeping the shutter open and to obtain a frame in synchronization with a goniometer. For example, each of non-patent documents 1 to 3 describes a semiconductor pixel detector which can obtain diffraction data in a continuous mode without opening and closing the shutter for each frame. In this semiconductor pixel detector, when crystal rotation starts, electronic control of the detector is used as a shutter and an image is recorded continuously, and therefore synchronization of opening and closing in the mechanical shutter is not necessary. By using the semiconductor pixel detector in this manner, it becomes possible to perform the shutter-less measurement which makes the shutter control unnecessary.

NON-PATENT DOCUMENT

Non-patent document 1: Kazuya Hasegawa, Kunio Hirata, Tetsuya Shimizu, Nobutaka Shimizu, Takaaki Hikima, Seiki Baba, Takeshi Kumasaka, and Masaki Yamamoto, "Development of a shutterless continuous rotation method using an X-ray CMOS detector for protein crystallography", International Union of Crystallography, Great Britain, Journal of Applied Crystallography, 14 Oct. 2009, Volume 42, p. 1165-1175

Non-patent document 2: Gregor Hulsen, Christian Broennimann, Eric F. Eikenberry and Armin Wagner "Protein crystallography with a novel large-area pixel detector", International Union of Crystallography, Great Britain, Journal of Applied Crystallography, 5 May 2006, Volume 39, p. 550-557

Non-patent document 3: Ch. Broennimann, E. F. Eikenberry, B. Henrich, R. Horisberger, G. Huelsen, E. Pohl, B. Schmitt, C. Schulze-Briese, M. Suzuki, T. Tomizaki, H. Toyokawa and A. Wagner "The PILATUS 1M detector", International Union of Crystallography, Great Britain, Journal of Synchrotron Radiation, 22 Nov. 2005, Volume 13, p. 120-130

Non-patent document 4: Shigeru Kosaki "Automatic Search Match of X-ray Diffraction Data" Progress of X-ray Analysis 13, Japan, Kagaku Gijutsu-Sha, 20 Nov. 1981, p. 47

PATENT DOCUMENT

Patent document 1: Japanese Patent Application Laid-Open Publication No. 2003-75373

Patent document 2: Japanese Patent Application Laid-Open Publication No. 08-338818

Patent document 3: Japanese Patent Application Laid-Open Publication No. 2003-149180

Figure 11:
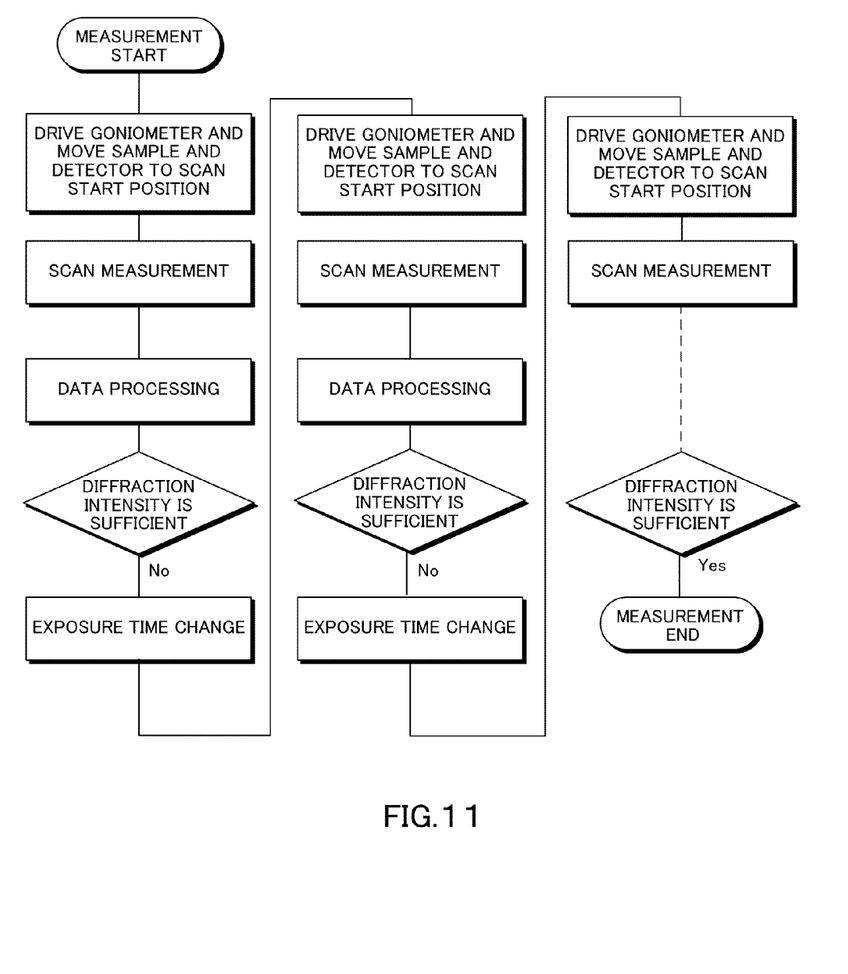
FIG. 11 is a flowchart showing operation of a conventional apparatus.

In the end, however, when a user sets the exposure time to measure the diffracted X-ray as described above and obtained diffraction intensity is not sufficient, the measurement needs to be performed again from the start. FIG. 11 is a flowchart showing the operation of a conventional apparatus. As shown in FIG. 11, when the diffraction intensity is not sufficient even after the scanning has been finished, re-measurement is repeated. Although, in order to avoid such a situation and to perform the measurement efficiently, the exposure time needs to be set first to be suitable for the diffraction intensity, such handling is extremely difficult.

SUMMARY OF THE INVENTION

The present invention has been achieved in view of such a situation and aims to provide an X-ray diffraction apparatus, an X-ray diffraction measuring method, and an control program, which can reduce the total exposure time and improve efficiency of the measurement.

(1) For achieving the above object, an X-ray diffraction apparatus of the present invention is an X-ray diffraction apparatus which irradiates a sample with an X-ray and performs frame photographing in each angle range, and includes a control section controlling the frame photographing by scanning without closing a shutter, a data acquisition section acquiring detection data of each frame which has been detected by a semiconductor pixel detector in the frame photographing, a frame integration section integrating the detection data acquired in each the scanning for each frame, and a determination section determining whether the integrated detection data has a sufficient intensity or not, wherein the control section controls so as to finish measurement when the integrated detection data has a sufficient intensity and so as to perform scanning again when the integrated detection data does not have a sufficient intensity.

In this manner, the X-ray diffraction apparatus of the present invention performs the scanning without closing the shutter, integrates the data without scanning again from the start, finishes the measurement when the integrated detection data has a sufficient intensity, and otherwise performs the frame photographing again to integrate the detected data. Thereby, it is possible to reduce the total exposure time and to improve efficiency of the measurement.

(2) Moreover, the X-ray diffraction apparatus of the present invention further includes an exposure time calculation section calculating a necessary total exposure time and an exposure time in the next and succeeding scanning according to the acquired detection data, after the scanning has been performed for the first time, wherein the control section controls the next and succeeding scanning using the calculated exposure time. Thereby, it is possible to optimize the exposure time and to measure the intensity of the detection data necessary for analysis in a minimum time.

(3) Moreover, in the X-ray diffraction apparatus of the present invention, the frame integration section corrects the acquired detection data at each pixel in each frame, multiplies the corrected detection data with a predetermined coefficient, and integrates the multiplied value after rounding-off. Thereby, it is possible to reduce an error which propagates through calculation process of the detection data.

(4) Moreover, the X-ray diffraction apparatus of the present invention further includes a coefficient calculation section calculating the predetermined coefficient according to the acquired detection data, after the scanning has been performed for the first time. Thereby, it is possible to calculate an optimal coefficient first for reducing the error.

(5) An X-ray diffraction measuring method of the present invention is an X-ray diffraction measuring method which irradiates a sample with an X-ray and performs frame photographing in each angle range, and includes the steps of controlling the frame photographing by scanning without closing a shutter, acquiring detection data of each frame which has been detected by a semiconductor pixel detector in the frame photographing, correcting the detection data acquired in each the scanning at each pixel and integrating the corrected detection data for each frame, determining whether the integrated detection data has a sufficient intensity or not, and controlling so as to finish measurement when the integrated detection data has a sufficient intensity and so as to perform the scanning again when the integrated detection data does not have a sufficient intensity. Thereby, it becomes possible to optimize the exposure time and to perform highly efficient photographing.

(6) A control program of the present invention is a control program which irradiates a sample with an X-ray and controls X-ray diffraction measurement using data obtained by frame photographing in each angle range, and causes a computer to execute processing including controlling the frame photographing by scanning without closing a shutter, acquiring detection data of each frame which has been detected by a semiconductor pixel detector in the frame photographing, correcting the detection data acquired in each the scanning at each pixel and integrating the corrected detection data for each frame, determining whether the integrated detection data has a sufficient intensity or not, and performing control so as to finish measurement when the integrated detection data has a sufficient intensity and so as to perform the scanning again when the integrated detection data does not have a sufficient intensity. Thereby, it becomes possible to optimize the exposure time and to perform highly efficient photographing.

According to the present invention, the X-ray diffraction apparatus performs scanning without closing a shutter, integrates data without the scanning again from the start, and finishes the measurement when the integrated detection data has a sufficient intensity and otherwise performs frame photographing again to integrate the detection data. As a result, it is possible to reduce the total exposure time and to improve efficiency of the measurement.

BRIEF DESCRIPTION OF DRAWINGS

FIG. 9 is a table showing a relationship between an exposure time and R and the like.

DETAILED DESCRIPTION OF THE INVENTION

Next, embodiments of the present invention will be explained with reference to the drawings. For easy understanding of the explanation, the same constituent is provided with the same reference numeral in each of the drawings and duplicated explanation will be omitted.

First Embodiment

Configuration of an X-Ray Diffraction Apparatus

Figure 1:
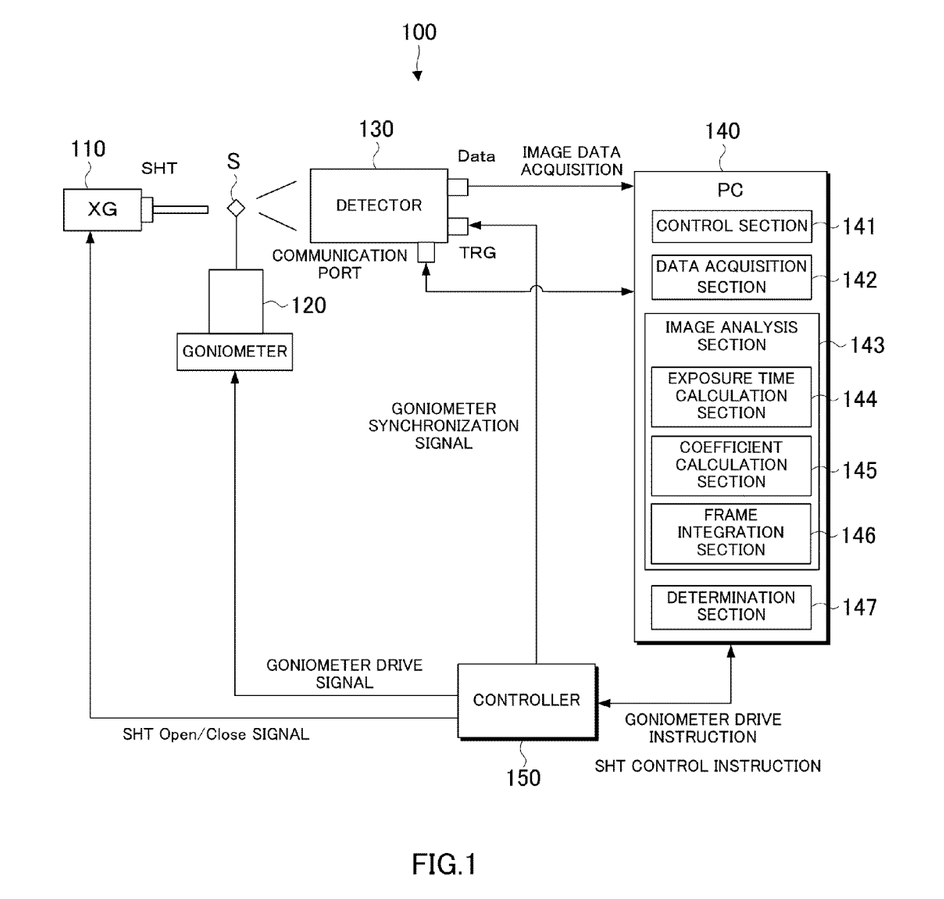
FIG. 1 is a diagram showing a schematic configuration of an X-ray diffraction apparatus of the present invention.
Figure 2:
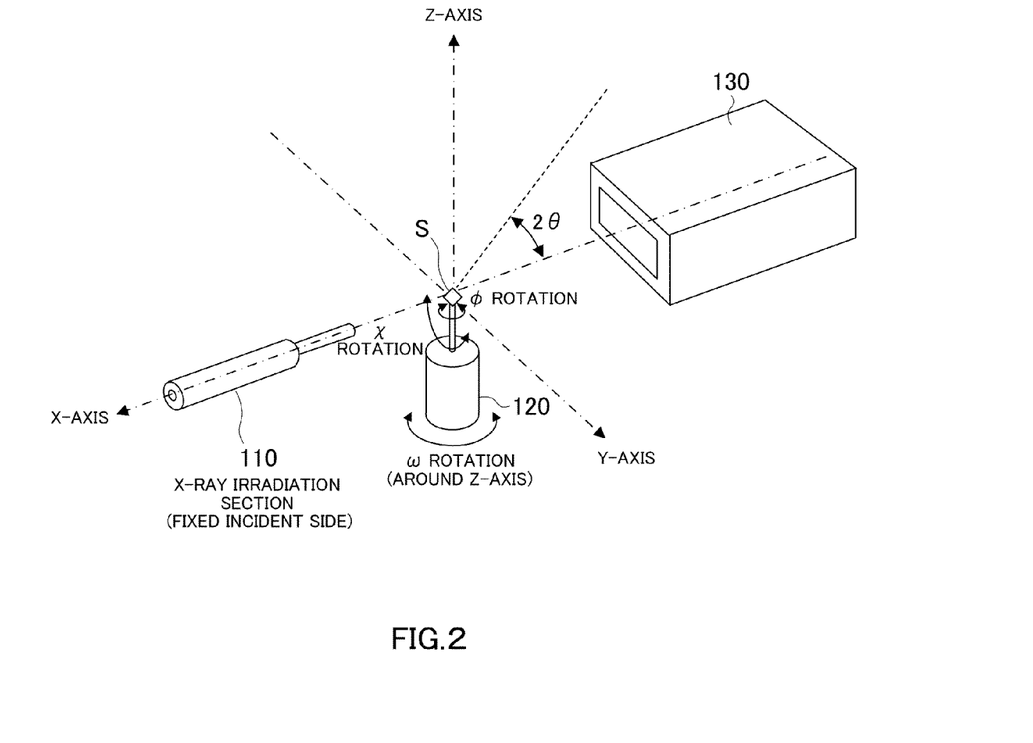
FIG. 2 is a perspective view showing a measurement system of the present invention.

FIG. 1 is a diagram showing a schematic configuration of an X-ray diffraction apparatus 100. Further, FIG. 2 is a perspective view of a measurement system. The X-ray diffraction apparatus 100 is an apparatus which irradiates a sample S with an X-ray and performs frame photographing in each angle range. The X-ray diffraction apparatus 100 includes an X-ray irradiation section 110, a sample support section 120, a detector 130, a computer 140, and a controller 150.

The X-ray irradiation section 110 collimates a characteristic X-ray (incident X-ray) narrowly and irradiates the sample S. The X-ray irradiation section 110 is not moved but fixed in the present embodiment. An Mo target or the like is used for an X-ray source. Further, a monochrometer is disposed and the X-ray is converted into a single line ray of Kα line. The X-ray irradiation section 110 includes a shutter, and opens or closes the shutter on receiving a shutter opening and closing signal from the controller 150 at the start or the end of scanning. Here, the scanning means measurement in which the X-ray incident direction is moved at a constant speed across a target angle range and frame photographing is performed for each of certain angle steps. Further, the frame photographing means a photographing which integrates frame data detected by one shot.

The sample support section 120 includes a stage where the sample S of a single crystal can be disposed, and can adjust the χ and φ rotation positions and the x, y, and z positions of the sample S. Further, a goniometer can drive the sample support section 120 in the ω direction (rotation direction around the Z-axis) on receiving a drive signal from the controller 150.

The detector 130 is a pixel type semiconductor detector capable of shutter-less photographing which makes shutter control unnecessary, and the detector 130 is disposed capable of driving in a diffraction angle (2θ) direction (rotation direction around the Z-axis). The detector 130 receives a goniometer synchronization signal from the controller 150 and enable the frame photographing in synchronization with the rotation of the sample support section 120.

The computer 140 mounts a CPU and a memory, and executes a program which controls the measurement system. A personal computer is used for the computer 140, for example. The computer 140 includes a control section 141, a data acquisition section 142, an image analysis section 143, and a determination section 147. Further, the image analysis section 143 includes an exposure time calculation section 144, a coefficient calculation section 145, and a frame integration section 146.

The control section 141 controls the frame photographing in each angle range by moving the sample support section 120 and the detector 130 to perform the scanning without closing the shutter. In this manner, the scanning without closing the shutter enables highly efficient photographing.

Further, the control section 141 controls so as to finish the measurement when the integrated detection data has a sufficient X-ray intensity and so as to perform the scanning again when the integrated detection data does not have a sufficient intensity, according to a determination result of the determination section 147. Thereby, when the intensity is insufficient, it is possible to proceed with the measurement by scanning repeatedly and obtaining the integrated detection data. As a result, it is possible to reduce the exposure time required for the whole measurement and to improve efficiency of the measurement.

The data acquisition section 142 takes into the computer 140 the detection data of each frame which has been detected by the detector 130 in the frame photographing. The detection data is image data expressing intensity distribution of pixels in each frame.

The exposure time calculation section 144 calculates a necessary total exposure time and an exposure time for the next and succeeding scanning according to the detection data acquired in the first scanning. Accordingly, the control section 141 controls the next and succeeding scanning using the calculated exposure time. Thereby, it is possible to optimize the exposure time and to measure the intensity of the detection data necessary for the analysis in a minimum time.

The coefficient calculation section 145 calculates the predetermined coefficient (multiplication value n) according to the acquired detection data, after the scanning has been performed for the first time. Thereby, it is possible to calculate the optimal coefficient for reducing an error. Note that the detail of an embodiment using the coefficient will be described below.

The frame integration section 146 integrates the detection data of each frame which has been acquired by the scanning, for each frame. The frame integration section 146 corrects the acquired detection data at each pixel in each frame and integrates the value of the corrected detection data after rounding-off. For example, when the integrated intensity is not sufficient in the first scanning, the second scanning is performed, and the frame data of each angle range in the first scanning and the frame data detected for the same angle range in the second scanning are integrated with each other.

The determination section 147 determines whether the integrated detection data has a sufficient intensity or not. Specifically, whether it has a sufficient intensity or not is determined depending on whether or not the average intensity value of the integrated detection data is a predetermined reference value or more. For the intensity to be determined, it is preferable to obtain the average value of pixel intensities in each frame. Here, the predetermined reference value is a value which is determined empirically and preferably set in advance. By such determination, it is possible to repeat the scanning as required and it becomes unnecessary to perform the scanning again from the start, which leads to reduction of the measurement time.

(Operation of the X-Ray Diffraction Apparatus)

Figure 3:
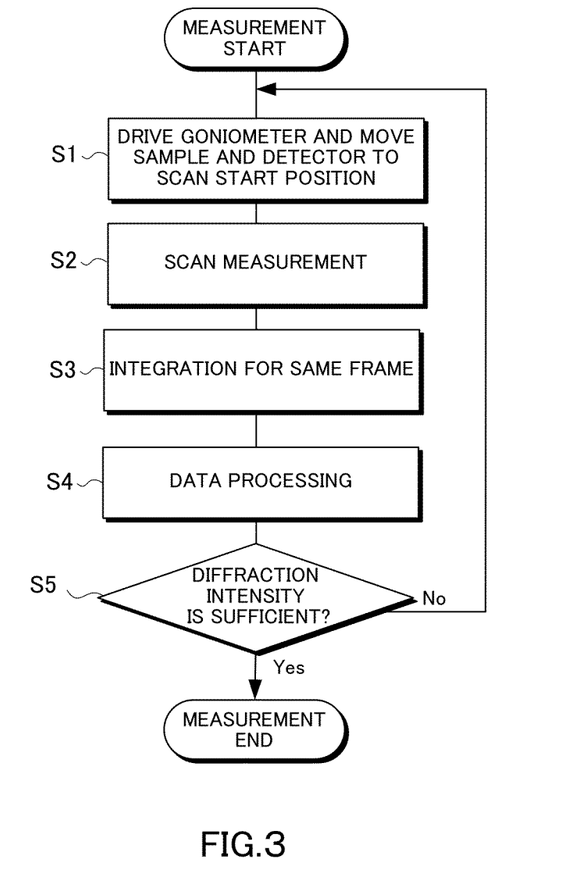
FIG. 3 is a flowchart showing operation of an X-ray diffraction apparatus according to a first embodiment.
Figure 4:
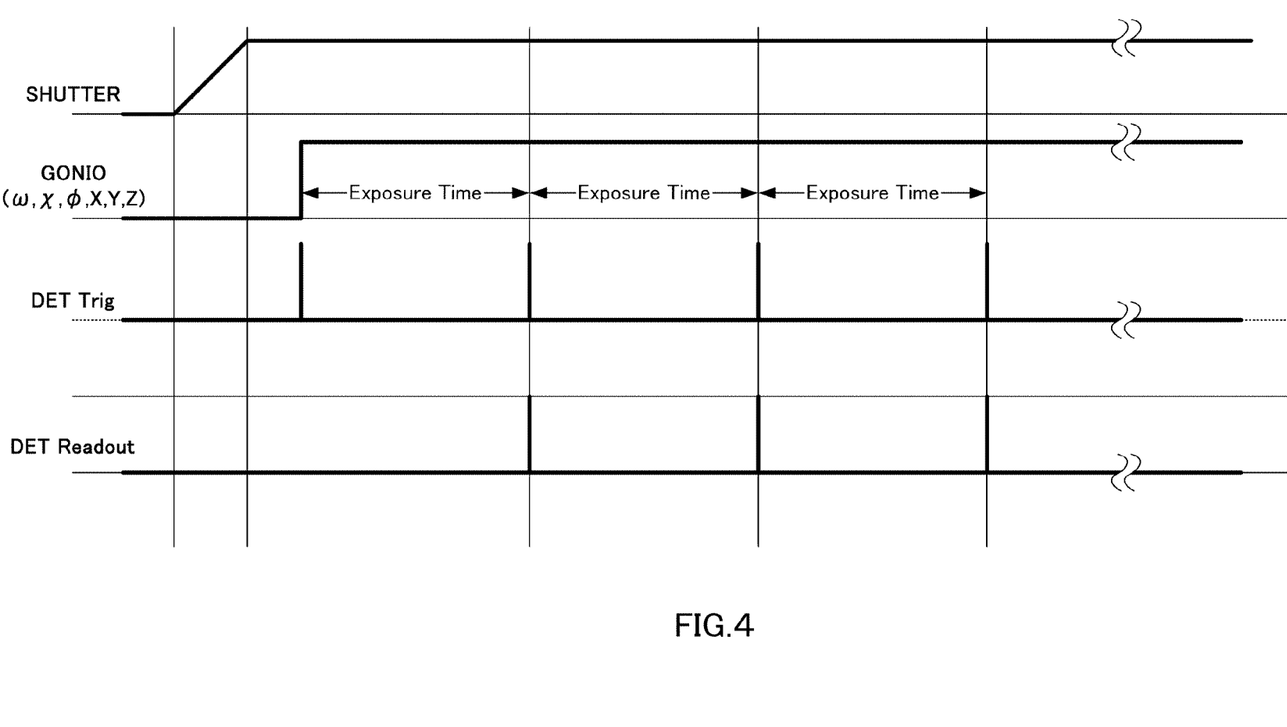
FIG. 4 is a diagram showing a measurement sequence for several frames in the present invention.
Figure 5:
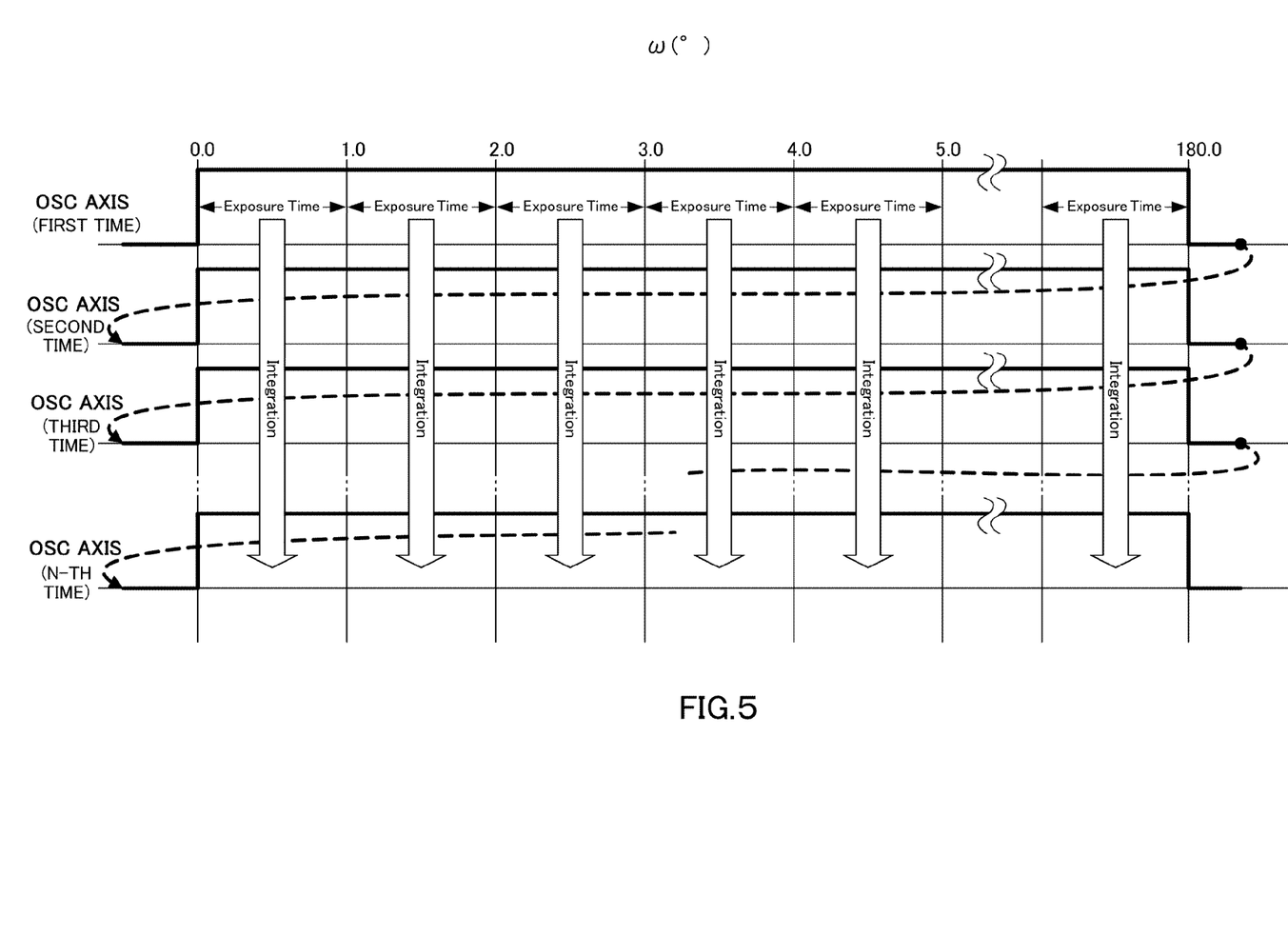
FIG. 5 is a diagram showing an example of a measurement sequence up to the n-th scanning.

The operation of the X-ray diffraction apparatus 100 configured as above will be explained. FIG. 3 is a flowchart showing the operation of the X-ray diffraction apparatus 100. Further, FIG. 4 is a diagram showing a measurement sequence for several frames. Moreover, FIG. 5 is a diagram showing an example of a measurement sequence up to the n-th scanning. Here, the period shown in FIG. 4 as "exposure time" corresponds to one frame photographing. DET trig in FIG. 4 is a trigger signal for starting detection in the detector 130, and DET Readout is a signal for starting readout operation of the detector 130.

First, the goniometer is driven and the sample S and the detector 130 are moved to a scanning start position (step S1), and the scan measurement is started (step S2). At this time, the frame photographing is performed continuously by the scanning without closing the shutter. Then, the frame intensity of the same diffraction angle is integrated (step S3). Note that, in the first scanning, while substantially the detection data is obtained just by the scan, this could be also understood as the detection data is integrated with zero intensity. In the example shown in FIG. 5, 2θ is changed from 0 to 180 degrees for one scan.

Next, the computer 140 acquires the detection data of each frame which has been integrated in the same frame by the detector 130. Then, the detection data acquired in each scanning is corrected at each pixel, and the corrected detection data is integrated for each frame.

The detection data integrated in this manner is data-processed, and an average pixel intensity value is calculated for each frame (step S4). Then, it is determined whether the diffraction intensity is sufficient or not, by determining whether or not the average intensity value is a predetermined reference value or more (step S5).

When the integrated detection data has a sufficient intensity, the measurement is finished, and, when the integrated detection data does not have a sufficient intensity, the measurement is returned to step S1 and the scanning is performed again. In the example of sequence shown in FIG. 5, repeated scanning is performed up to the n-th time. By such control, it is possible to optimize the whole exposure time across the measurement and to improve efficiency of the measurement. Note that it is possible to realize the above operation by causing the computer 140 to execute a program.

Second Embodiment

Method of Reducing Rounding-Off Effect

In the processing of the detection data, rounding-off (approximation) of a numerical value is performed according to any rule such as rounding half up, rounding down, and rounding up, and the detection data is corrected at each pixel and the rounded value is integrated as it is, in the above embodiment. For this operation, it is preferable to multiply the detection data with a predetermined coefficient before the rounding-off.

In the present embodiment, the frame integration section 146 corrects the acquired detection data at each pixel in each frame, multiplies the corrected detection data with the predetermined coefficient, and integrates the obtained value after rounding-off. Thereby, it is possible to reduce an error propagating through the detection data calculation process. Note that the multiplication of the detection data with the coefficient is not necessarily performed by the frame integration section 146 but may be performed in the detector 130.

(Operation of the X-Ray Diffraction Apparatus)

Figure 6:
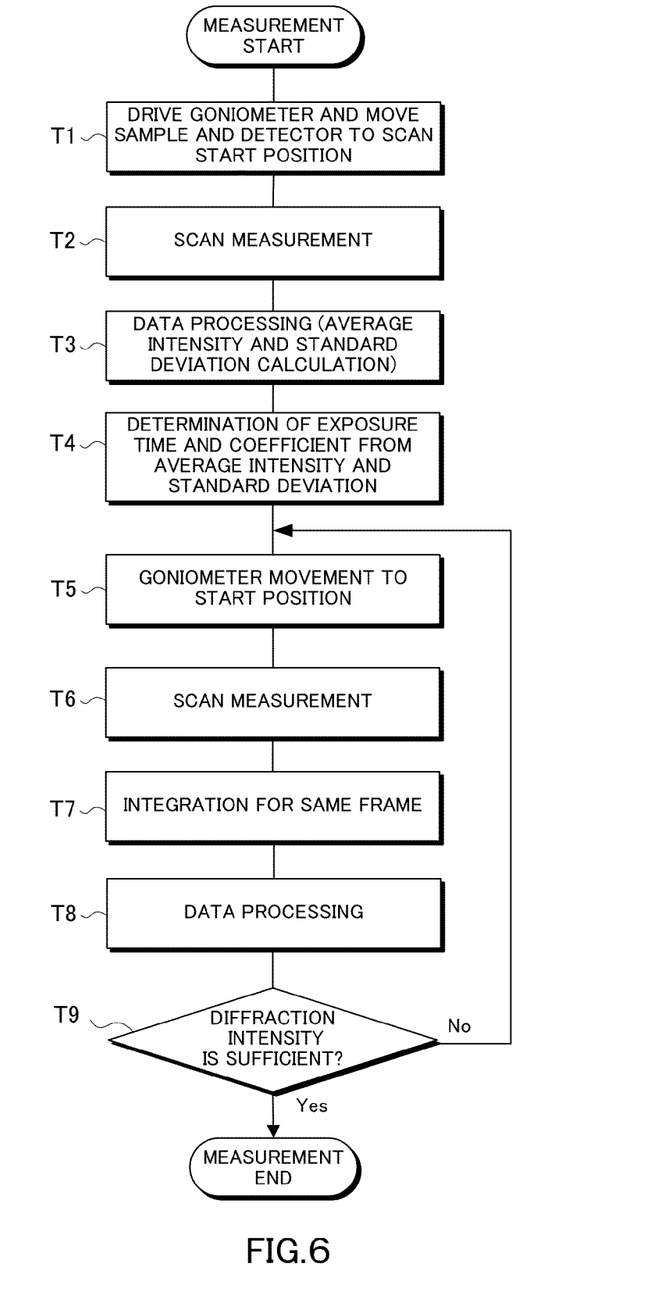
FIG. 6 is a flowchart showing operation of an X-ray diffraction apparatus according to a second embodiment.

When the detection data is multiplied with the coefficient, it is preferable to determine the coefficient and the exposure time of one frame in the first scanning. FIG. 6 is a flowchart showing the operation of the X-ray diffraction apparatus 100.

As shown in FIG. 6, first, the X-ray diffraction apparatus 100 drives the goniometer to move the sample S and the detector 130 to a start point of the scanning (step T1), and starts the first scanning (step T2). Then, the X-ray diffraction apparatus 100 processes the detection data obtained in the first scanning, calculates the average intensity and the standard deviation (o) of pixels in each frame (step T3), determines the exposure time and the coefficient (multiplication value n) from the obtained average intensity and the standard deviation (step T4).

Next, the X-ray diffraction apparatus 100 drives the goniometer to move the sample S and the detector 130 to the start point of the scanning (step T5). Then, the scanning is performed using the calculated exposure time (step T6). The detection data is corrected, multiplied with the coefficient, and integrated for the frame of the same diffraction angle (step T7), and the average value for the pixels is calculated from the integrated detection data (step T8). Then, it is determined whether the diffraction intensity is sufficient or not, using the average value (step T9). When the diffraction intensity is not sufficient, the measurement is returned to step T5 and the scanning is performed again, and, when the diffraction intensity is sufficient, the measurement is finished.

Example

Figure 7:
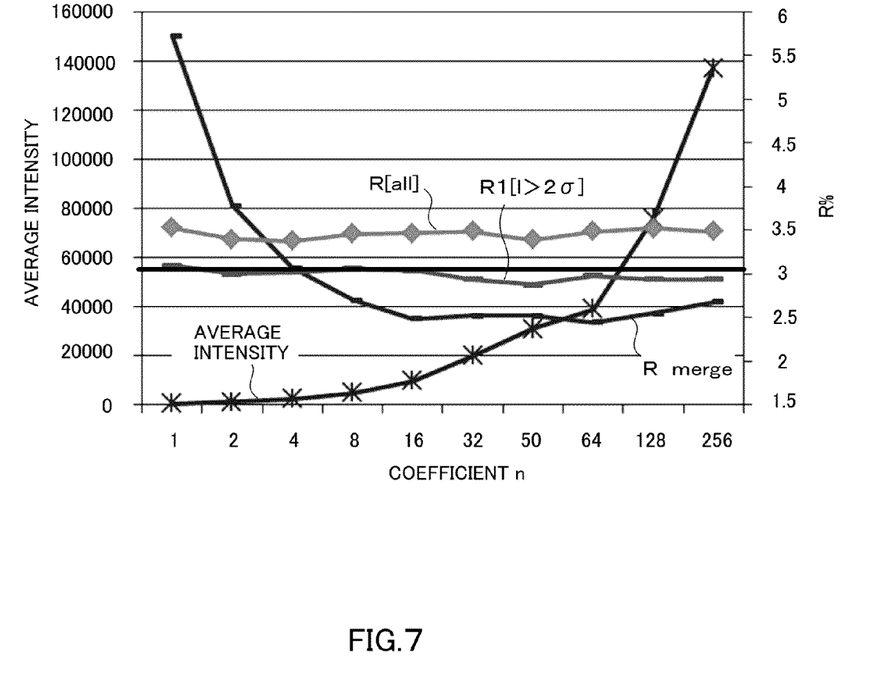
FIG. 7 is a diagram showing a detection data average value, R1, Rmerge, and R with respect to a coefficient n for an exposure time of 16 sec.
Figure 8:
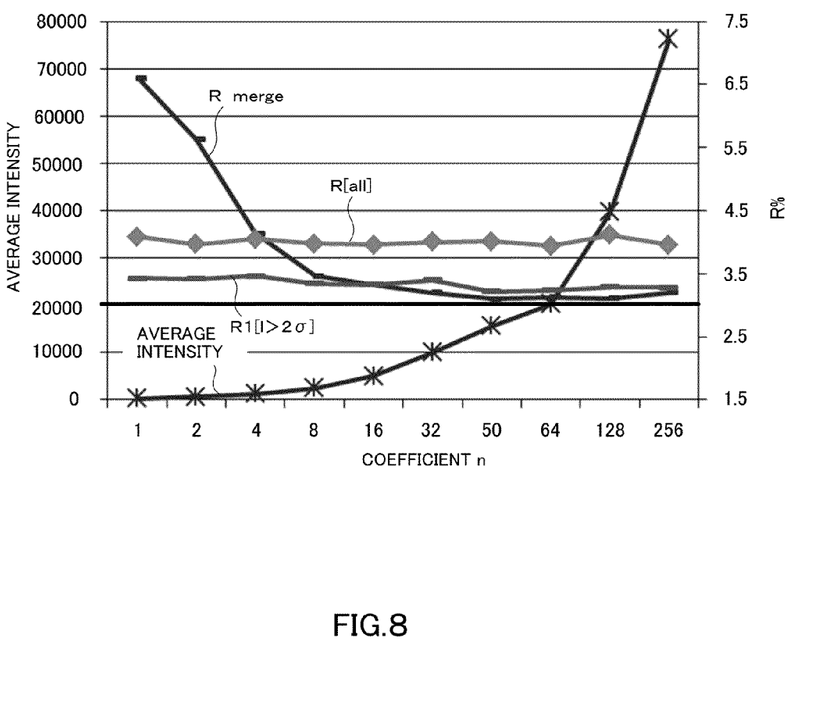
FIG. 8 is a diagram showing a detection data average value, R1, Rmerge, and R with respect to a coefficient n for an exposure time of 8 sec.

X-ray diffraction measurement of a single crystal sample was performed by the above method as shown in FIG. 6, for exposure times of 16 sec and 8 sec. Then, the average intensity, R1, Rmerge, and R were obtained with respect to the coefficient for the detection data in each measurement. Each of R1, Rmerge, and R is an index showing accuracy of the intensity value, Rmerge shows an intensity error of equivalent reflectance for the measurement data, and each of R and R1 shows an error between a measured value and a theoretical value of a structure analysis result. FIG. 7 is a diagram showing the average intensity, R1, Rmerge, and R of the detection data with respect to the coefficient n for an exposure time of 16 sec. FIG. 8 is a diagram showing the average intensity, R1, Rmerge, and R of the detection data with respect to the coefficient n for an exposure time of 8 sec. In either case of FIG. 7 and FIG. 8, Rmerge becomes smaller as the coefficient is increased in a range of the coefficient n from 1 to around 128. Further, R also tends to become slightly smaller.

Figure 9:
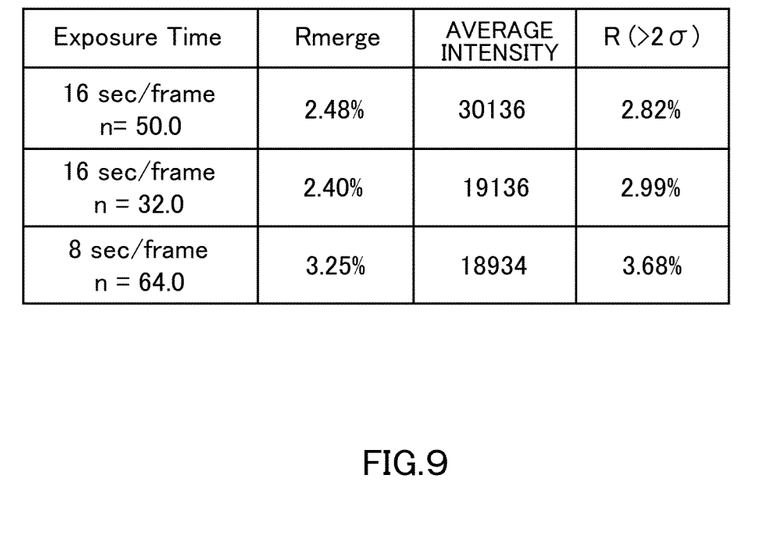

FIG. 9 is a table showing a relationship between the exposure time and Rmerge and R. As shown in FIG. 9, when the exposure time is set to 16 sec, R decreased to have a small value as a value less than 3% for either coefficient n of 50 and 32. Further, also when the exposure time is set to 8 sec, R decreased to have a small value as a value in the order of 3% for a coefficient n of 64. From such results, it has been verified that, also when the diffraction intensity is measured efficiently, it is possible to reduce R by setting the coefficient n to an appropriate value according to the exposure time.

What is claimed is:

1. An X-ray diffraction apparatus with a shutter which irradiates a sample with an X-ray and performs frame photographing in each rotation angle range, comprising: a control section controlling the frame photographing in each rotation angle range by scanning without closing the shutter of the x-ray diffraction apparatus; a data acquisition section acquiring detection data of each frame which has been detected by a semiconductor pixel detector in the frame photographing; a frame integration section integrating the detection data acquired in each the scanning for the same frame; and a determination section determining whether the integrated detection data has a sufficient intensity or not, wherein the control section controls so as to finish measurement when the integrated detection data has a sufficient intensity and so as to perform scanning again when the integrated detection data does not have a sufficient intensity.

2. The X-ray diffraction apparatus according to claim 1, further comprising
an exposure time calculation section calculating a necessary total exposure time and an exposure time in the next and succeeding scanning according to the acquired detection data, after the scanning has been performed for the first time, wherein
the control section controls the next and succeeding scanning using the calculated exposure time.

3. The X-ray diffraction apparatus according to claim 1, wherein
the frame integration section corrects the acquired detection data at each pixel for each frame, multiplies the corrected detection data with a predetermined coefficient, and integrates the multiplied value after rounding-off.

4. The X-ray diffraction apparatus according to claim 3, further comprising
a coefficient calculation section calculating the predetermined coefficient according to the acquired detection data, after the scanning has been performed for the first time.

5. An X-ray diffraction measuring method utilizing a shutter which irradiates a sample with an X-ray and performs frame photographing in each rotation angle range, comprising the steps of: controlling the frame photographing in each rotation angle range by scanning without closing the shutter; acquiring detection data of each frame which has been detected by a semiconductor pixel detector in the frame photographing; correcting the detection data acquired in each the scanning at each pixel, and integrating the corrected detection data for each frame; determining whether the integrated detection data has a sufficient intensity or not; and controlling so as to finish measurement when the integrated detection data has a sufficient intensity and so as to perform the scanning again when the integrated detection data does not have a sufficient intensity.

6. A computer-readable non-transitory recording medium recording a control program which controls irradiation of a sample, utilizing a shutter, with an X-ray and controls X-ray diffraction measurement using data obtained by frame photographing in each rotation angle range, the control program causing a computer to execute processing comprising: controlling the frame photographing in each rotation angle range by performing scanning without closing the shutter; acquiring detection data of each frame which has been detected by a semiconductor pixel detector in the frame photographing; correcting the detection data acquired in each the scanning at each pixel and integrating the corrected detection data for each frame, determining whether the integrated detection data has a sufficient intensity or not, and controlling so as to finish measurement when the integrated detection data has a sufficient intensity and so as to perform the scanning again when the integrated detection data does not have a sufficient intensity.

\* \* \* \* \*